United States Patent [19]

Harnly et al.

[11] Patent Number: 5,018,856
[45] Date of Patent: May 28, 1991

[54] CONTINUUM SOURCE ATOMIC ABSORPTION SPECTROMETRY

[75] Inventors: James M. Harnly, Bethesda; Gary P. Moulton, Germantown; Thomas C. O'Haver, Silver Spring, all of Md.

[73] Assignees: The United States of America as represented by the Secretary of Agriculture, Washington, D.C.; The University of Maryland, College Park, Md.

[21] Appl. No.: 428,529

[22] Filed: Oct. 30, 1989

[51] Int. Cl.$^5$ .............................. G01J 3/30; G01J 3/40; G01J 3/28

[52] U.S. Cl. .................................. 356/312; 356/305; 356/328

[58] Field of Search ............... 356/328, 326, 311, 307, 356/305, 316

[56] References Cited

U.S. PATENT DOCUMENTS

| | | | |
|---|---|---|---|
| 3,472,594 | 10/1969 | Hughes et al. | 356/93 |
| 3,532,429 | 10/1970 | Hughes et al. | 356/95 |
| 3,588,252 | 6/1971 | Habosian | 356/82 |
| 3,752,585 | 8/1973 | Elliott | 356/98 |
| 3,822,098 | 7/1974 | Ruddler et al. | 356/209 |
| 3,901,599 | 8/1975 | Meric | 356/85 |
| 3,985,441 | 10/1976 | Schoeffel et al. | 356/88 |
| 4,030,828 | 6/1977 | Sonobe et al. | 356/96 |
| 4,049,353 | 9/1977 | Missio | 356/85 |
| 4,300,833 | 11/1981 | Harnly et al. | 356/307 |
| 4,462,685 | 7/1984 | Smith, Jr. et al. | 356/326 |
| 4,820,048 | 4/1989 | Barnard | 356/307 |
| 4,940,325 | 7/1990 | Becker-Ross et al. | 356/328 |

OTHER PUBLICATIONS

"A Microcomputer-Controlled Background Correction System for Atomic Spectrometry", O'Haver et al., Analyst, May 1985, vol. 110.
"Design and Construction of a Time Multiplex Multiple Slit, Multielement Flame Atomic Absorption Spectrometer", Salin et al., Analytical Chemistry, Nov. 1978, vol. 50, No. 13.
Chuang, F. S. et al., Anal. Chem., 50, 525-530 (1978).
Coddling, E. G. et al., Anal. Chem., 52, 2133-2140 (1980).
Oldham et al., Anal. Instr., 16(2), 263-274 (1987).
Chinnock, R., ILC Engineering Note, No. 152, May 1982, 24 pp., ILC Tech., Sunnyvale, Calif.
Retzik, M. et al., "Concept and Design of a Simultaneous Multielement . . . ", Am. Lab., Sep. (1987), pp. 70-77.
McGeorge, Scott W., "Imaging Systems: Detectors of the Past . . . ", Spectroscopy, vol. 2, No. 4, 1987.
Description of McPherson Optical Systems, pp. A1 and A2, McPherson, Acton, Mass.
Skogerboe, R. K. et al., "A Dynamic Background Correction. . . ", Applied Sp., vol. 30, No. 5, 1976, pp. 495-500.
Epstein, M. S. et al., "Wavelength Modulation for . . . ", Applied Spect., vol. 30, No. 3, 1976, pp. 324-329.
CRIS Report, "Improved Instrumental Tech. for the Det. of Trace Metals", Proj. 0142504, placed on line 10/15/87.
CRIS Report, "Atomic Absorption Using a Pulsed continuum . . . ", Project 0142084, placed on line 5/26/87.

Primary Examiner—F. L. Evans
Assistant Examiner—K. P. Hantis
Attorney, Agent, or Firm—David R. Sadowski; M. Howard Silverstein

[57] ABSTRACT

The instant invention relates to a process and apparatus for atomic absorption analysis, utilizing: atomization of a sample (containing one or more elements), illuminating the atomized sample with a continuum light source to produce a resultant light, directing the resultant light through a light dispersing means, detection of light at the focal plane of the light dispersing means using an integrating array detector (e.g. linear photodiode array) for converting the incident light into amplified electrical signals, blocking the incident light from striking the detector means and during this blocking utilizing the detector means to convert integrated intensities into amplified electrical signals, and deriving from these signals a value proportional to concentration. The present invention permits the aforementioned analysis to be performed at a very high rate i.e. at least 40 times per second.

16 Claims, 4 Drawing Sheets

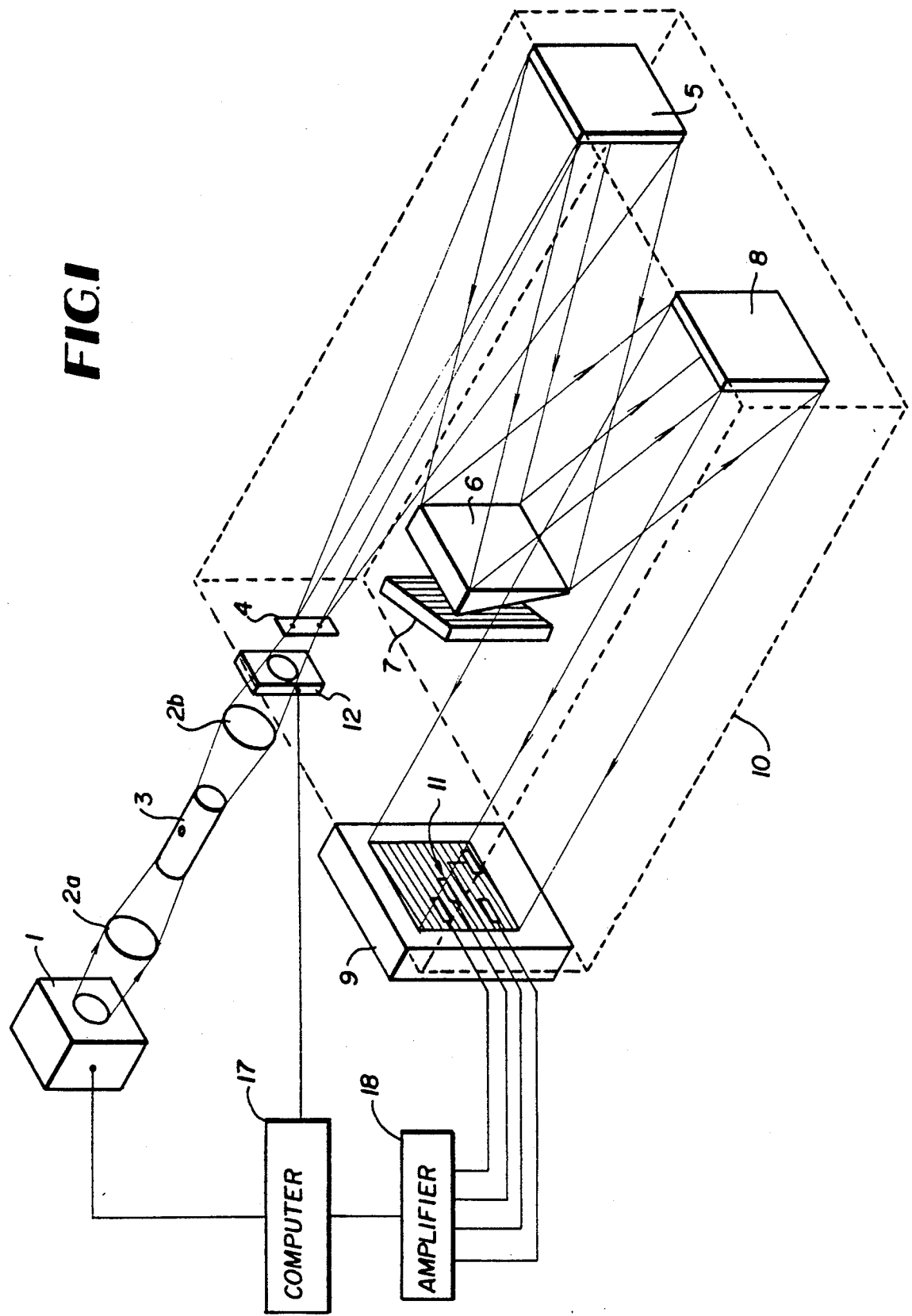

DETECTING COMPONENTS
OF ARRAY DETECTOR

CONTINUUM SOURCE ATOMIC ABSORPTION SPECTROMETRY

FIELD OF THE INVENTION

The present invention relates to dispersed light spectroscopy, specifically continuum source atomic absorption spectroscopy.

BACKGROUND AND SUMMARY OF THE INVENTION

Today, trace metals are being determined at the ultratrace level (part per billion concentration). Existing systems make accurate determinations at these levels laborious and predominantly single element processes, as typified by current commercially available atomic absorption spectroscopy (AAS) instruments. These instruments use a different light source (hollow cathode lamp (HCL)) for each element. Initial attempts at a multielement system used combinations of hollow cathode lamps and very large polychromators typically used for arc or spark source emission spectroscopy. The combined sources were inadequate, and the read out devices were bulky and cumbersome. The next generation of attempts, as exemplified by F. S. Chauang et al in Anal. Chem., 50, 525–530, (1978) and E. G. Codding et al in Anal. Chem., 52, 2133–2140 (1980), used similar combinations of HCLs with a linear photodiode array as a detector for conventional monochromators. The diode array was used to cover the largest wavelength possible (30 to 200 nanometers). The resulting instruments gave poor detection limits and were limited by the size of the array to analysis of only a few elements simultaneously. By contrast the present invention provides state of the art detection limits, and great versatility in the selection of elements to be analyzed simultaneously.

Another previous system is described in U.S. Pat. No. 4,300,833 issued 11/17/81 to Harnley et al, which employed a continuum source with mechanical wavelength scanning, a high dispersion polychromator, and photomultiplier tube detection for multielement absorption measurements. This system achieved simultaneous determination of 16 elements, excellent background correction, large calibration ranges, and state of the art detection limits for all elements with analytical wavelength above 300 nm. However, below 300 nm detection limits (signal-to-noise ratios) were worse than state of the art, because continuum sources have a reduced output in this region. This is a disadvantage of notable consequence because approximately one third of elements of interest have analytical wave lengths in this region (185 to 300 nm). It has surprisingly and unexpected been discovered, that by utilization of the present invention, all of the aforementioned advantages may be achieved along with greatly improved detection limits below 300 nanometers (nm).

Oldham et al in Anal. Instr., 16, 263-274 (1987) describe a system employing a modulated continuum source and a diode array (typically covering a 200–400 nm range) as a HPLC detector for molecular absorption. Oldham's purpose in modulating the source was to stabilize the lamp to avoid the flicker component i.e. no attempt was made to increase the intensity of the lamp.

ILC Engineering Note #152, "Use of Xenon Short ARCS as Pulsed Light Sources", ILC Technology, Sunnyvale, Calif., May, 1982, describes high energy burst mode of operation of the lamp, but it was used at very low duty cycles (1 to 2%) with the goal of achieving the maximum peak intensity.

A multielement (four channels) atomic absorption spectrometer is commercially available and is described in M. Retzik et al, "Concept and Design of a Simultaneous Multielement GF-AAS" in American Laboratory, Sept. (1987). Said spectrometer utilizes graphite furnace atomization, a bank of hollow cathode lamps, and two photo-multipliers for detectors, however it is limited to four elements at a time.

Another prior system disclosed in U.S. Pat. No. 4,049,353 to Missio employs light dispersing elements which may be utilized in the present invention. The system of Missio differs from the present invention in: (1) utilizing a plasma jet emission source as contrasted with the continuum source and electrothermal atomizer of the present invention, and; (2) utilizing an array of photomultiplier tubes in contrast with the integrating array detector means of the present invention. These distinctions permit the present invention to achieve measurements 1000 times more sensitive than the measurements made with the system of Missio.

The present invention avoids the aforementioned disadvantages of the prior art, and provides the surprising and unexpected advantages of:

using a continuum light source means (CLSM) and an integrating array detector means (IADM), said IADM dedicated to the measurement of light intensities over a short wavelength region e.g. of less than about five nm around the analytical wavelength of the element of interest;

using one or more IADMs to measure light intensities over a short wavelength region around the analytical wavelengths of a plurality of elements of interest;

using a burst mode of operation of the CLSM, said burst mode being exemplified by a lengthy idle period (e.g. of about 2 to 3 minutes) followed by a short time period (e.g. of about 10–15 seconds) of a series of short pulses (e.g. of about 1–5 milliseconds each) with an approximately 10–30% duty cycle, allowing the CLSM to exceed the maximum power rating by about 40–80%;

using a burst mode to give enhanced average source intensities over said short time period of a series of short pulses, by increasing the effective black body temperature of the CLSM and increasing the output intensity in the far ultraviolet region (as compared to a lamp operated in the direct current mode at a normal maximum power level) by pulsing the CLSM;

permitting said measured intensities over the short wavelength region to be converted to values proportional to concentration and independent of intensity as a function of time and wavelength;

the high quantum efficiency of the diode array, the multiplex advantage of observing the spectral region simultaneously, a large image width, and the enhanced intensity of the burst mode, resulting in an increased intensity throughput exceeding two orders of magnitude;

utilizing short length of each array, short source pulse, and high speed data acquisition to allow a high repetition rate of at least 40 times per second so that rapid, transient signals may be characterized;

a combination of the foregoing advantages providing a synergistic effect whereby a multielement atomic absorption spectrometer is created with state-of-the-art detection limits for trace metals at all wavelengths;

eliminating the need for a mechanical wavelength modulation device, allowing longer monitoring of each wavelength position, providing a higher quantum efficiency, and allowing better signal-to-noise ratios for trace metals with analytical lines in the far ultraviolet region, by use of an IADM.

These and other objects and advantages of the instant invention, which will become readily apparent from the ensuing description, are accomplished either individually or cumulatively by:

a process comprising, atomizing a sample to be analyzed; illuminating the atomized sample with a CLSM for emitting intensities from about 180 to about 800 nm, to produce a resultant light; directing the resultant light through a light dispersing means; detecting light simultaneously at more than one wavelength at a focal plane of the light dispersing means using an IADM, spanning a small wavelength region of about 4 to about 10 times the image width, for integrating with respect to time the amount of light incident thereon and for converting the incident light into amplified electrical signals proportional to the integrated intensities of the incident light; blocking the incident light from striking the detector means; during the step of blocking utilizing the detector means to convert integrated intensities into said signals; deriving from the amplified electrical signals a value proportional to concentration and independent of the intensity as a function of time and wavelength, and; repeating the steps of blocking and converting at a rate of at least 40 times per second, and;

an apparatus comprising, means for atomizing a sample to be analyzed; CLSM for illuminating the atomized sample with intensities from about 180 to about 800 nm; light dispersing means; light directing means for directing light from the CLSM through an atomized sample and into the light dispersing means; IADM, located at a focal plane of the light dispersing means, and spanning a wavelength region of about 4 to about 10 times the image width, for integrating with respect to time the amount of light incident thereon and for converting the incident light into amplified electrical signals proportional to the intensities of the incident light; means for blocking the incident light from striking the detector means; control means, operably associated with the means for blocking and the IADM, for controlling the means for blocking and for signaling the IADM to readout and for receiving from the IADM readout which is amplified electrical signals proportional to the integrated intensities, while incident light is blocked from striking the detector means; deriving means, operably associated with the IADM, for deriving from the amplified electrical signals a value proportional to concentration and independent of the intensity as a function of time and wavelength, and; wherein the means for blocking and control means function to provide their respective functions at a rate of at least 40 times per second.

BRIEF DESCRIPTION OF THE DRAWINGS

FIG. 1 illustrates one type of an echelle spectrometer which is a first embodiment of the present invention.

DESCRIPTION OF THE PREFERRED EMBODIMENTS

Figure 1A:
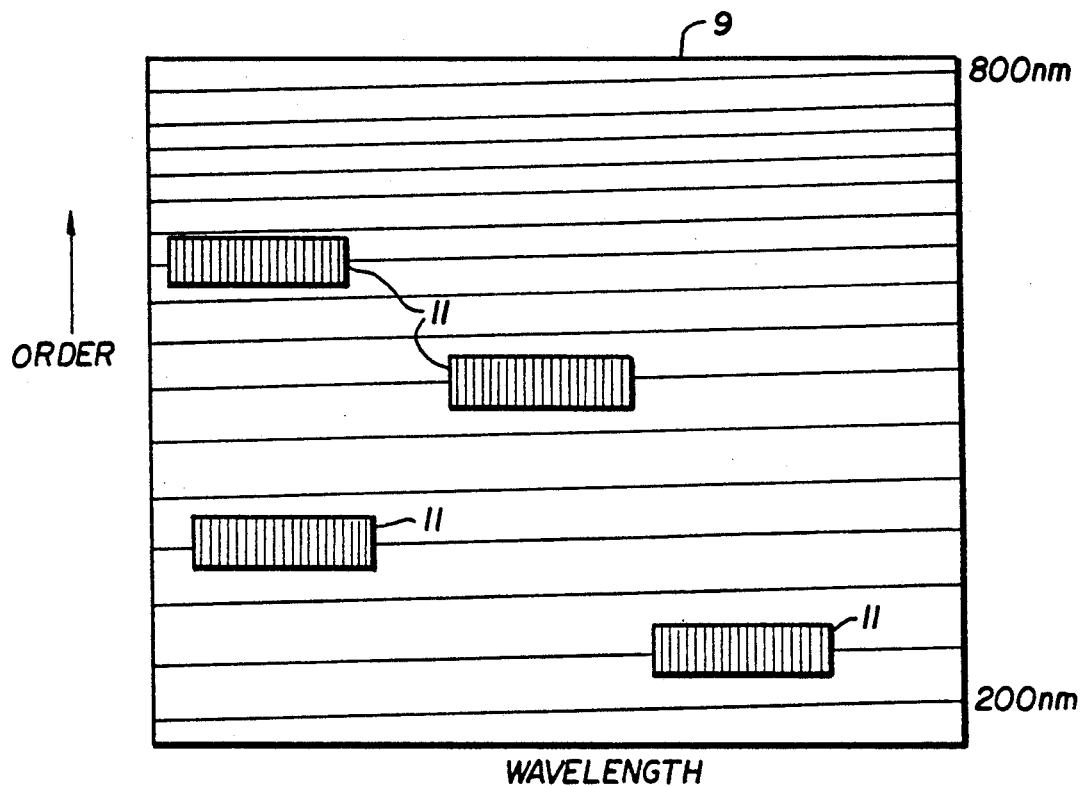
FIG. 1a shows in greater detail an example of the exit cassette of FIG. 1.

In the embodiment illustrated in FIG. 1, initially light is produced by a continuum light source means (CLSM) over a broad band spectrum i.e. emitting intensities from about 180 nm to about 800 nm. Examples of CLSM useable in the present invention include, Noble gas arc lamps, such as Cermax Xenon illuminators (xenon arc lamps) available from ILC technology, Sunnyvale, Calif. Light from the CLSM 1 is directed through a lens 2, which focuses the light through an atomizing means (3) for atomizing a sample (containing one or more elements) to be analyzed. Atomizing means suitable for use in the present invention include: an electrothermal furnace (e.g. graphite, tungstun, etc.), a flame atomizer, or a plasma generator (use of an electrothermal furnace being preferred). Subsequently, the resultant light passes from the atomizing means to a second lens designated 2b, by which the light is focused through shutter 12. It is preferred to employ a shutter with an aperture of ½ inch or less, and a response time (fully open to fully closed) of less than about 1 millisecond. The shutter functions as means for either permitting light to pass, or for blocking light from striking the detector means. Examples of suitable types of shutters include, an iris type device, a chopper, or a tuning fork. Thus in this embodiment the lenses constitute a light directing means for directing light from the continuum light source means 1 through an atomized sample and into the light dispersing means. Subsequently the light passes through an entrance slit 4 of the disperser/detector (i.e. light dispersing means and detector means) designated 10, to collimating mirror 5. This mirror collimates the light into parallel rays, which are directed through a prism 6 onto the Echelle defraction grating 7. This grating functions to defract the light at various angles according to wavelength, back through prism 6, and hence to focusing mirror 8. The light is focused by mirror 8 onto the exit cassette 9 located at the focal plane of the disperser/detector 10. The exit cassette has mounted thereon integrating array detector means (IADM) designated 11 in FIGS. 1 and 2 which: (1) spans a small wavelength region of about 4 to about 10 times the image width; (2) integrates with respect to time the amount of light incident thereon, and; (3) converts the incident light into amplified electrical signals proportional to the intensities of the incident light. Examples of such IADM include linear photodiode arrays (LPDA) and charge coupled devices (CCDs). The IADM may for example be a LPDA available from Hamamatsu Corp., Bridewater, N.J., and from EG and G, Reticon, Sunnyvale, Calif., or a CCD available from Photometrics Ltd., Tucson, Ariz. and EG and G Princeton Applied Research, Princeton, N.J. High fluctuation noise arising from the lack of reproducibility of the emitted pulses is eliminated by the simultaneous detection of the spectral region around the analytical wavelength, using a short diode array, and ratioing the intensities on and off the wavelength. Short arrays and fast read out rates allow sufficient time resolution to detect and characterize the rapid, transient signals from a graphite tube furnace. A series of IADMs are used for multielement detection; e.g. one IADM for each element. FIG. 1 also illustrates a computer 17 having electrical connection to: the CLSM 1; the shutter 12, and; the IADM via an amplifier 18.

FIG. 1A illustrates in greater detail the arrangement of the integrating array detector means (IADM) e.g. LPDAs or CCDs on the exit cassette 9. While for simplification of illustration only four IADMs are shown, it should be understood that a plurality of IADMs may be utilized, and the IADMs are located in a specific order containing the wavelength region of interest for each element i.e. each wavelength region is directed to one of the IADMs. Thus the present invention encompasses arranging the IADMs in, a linear configuration, a rectangular matrix or at separate specific regions of interest. The number of IADMs is only limited by the physical dimensions of the cassette.

Figure 2:
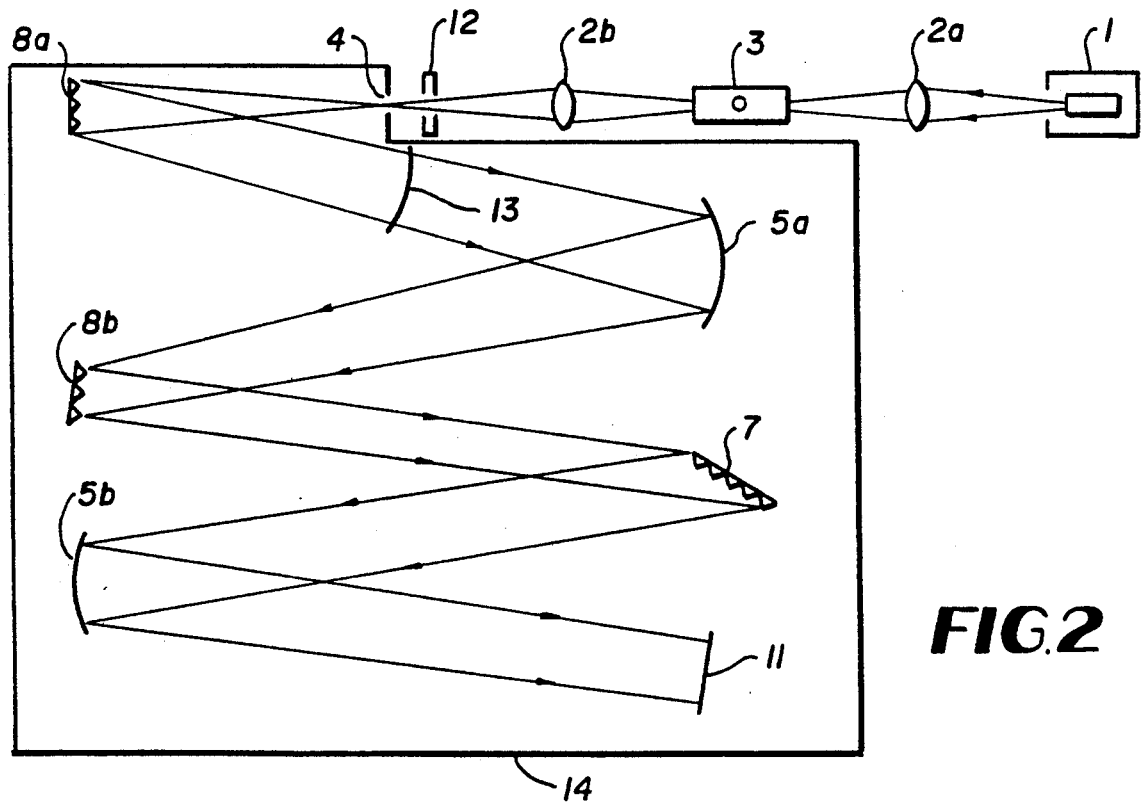
FIG. 2 depicts a second embodiment of the present invention, employing a monochromator with a mask and a following echell monochromator and a single IADM.
Figure 3:
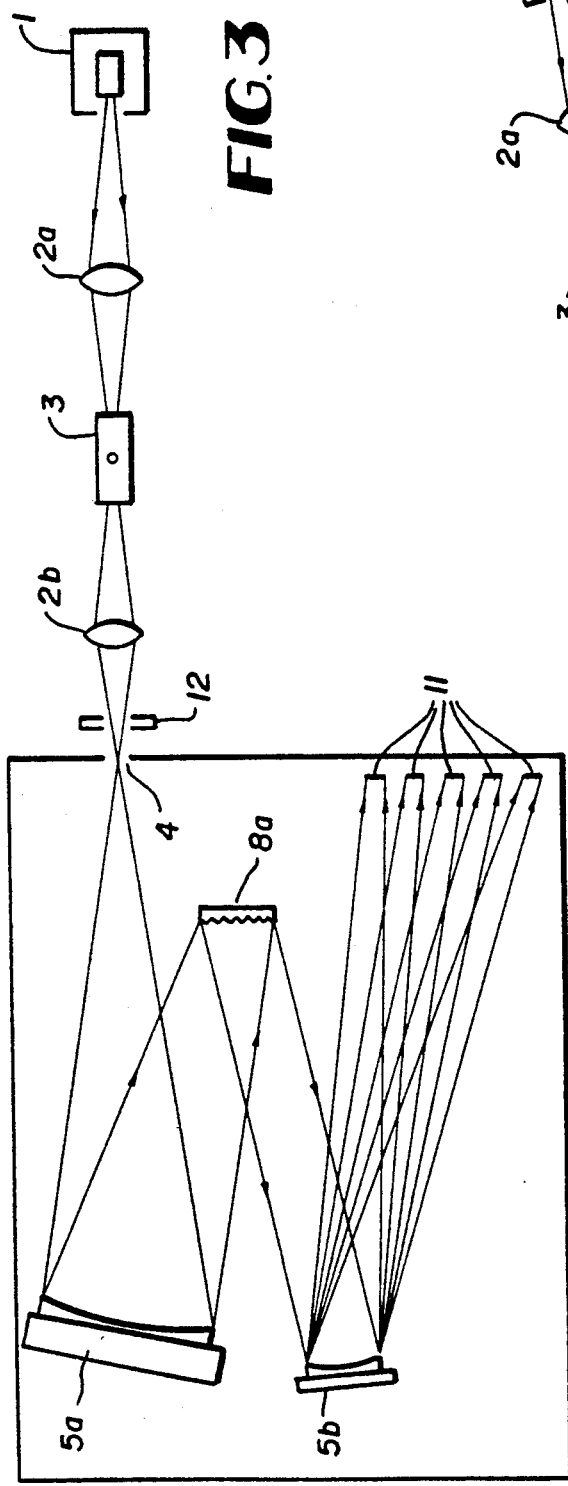
FIG. 3 illustrates a third embodiment of the present invention employing a corrected Loci type light dispersing system.
Figure 4:
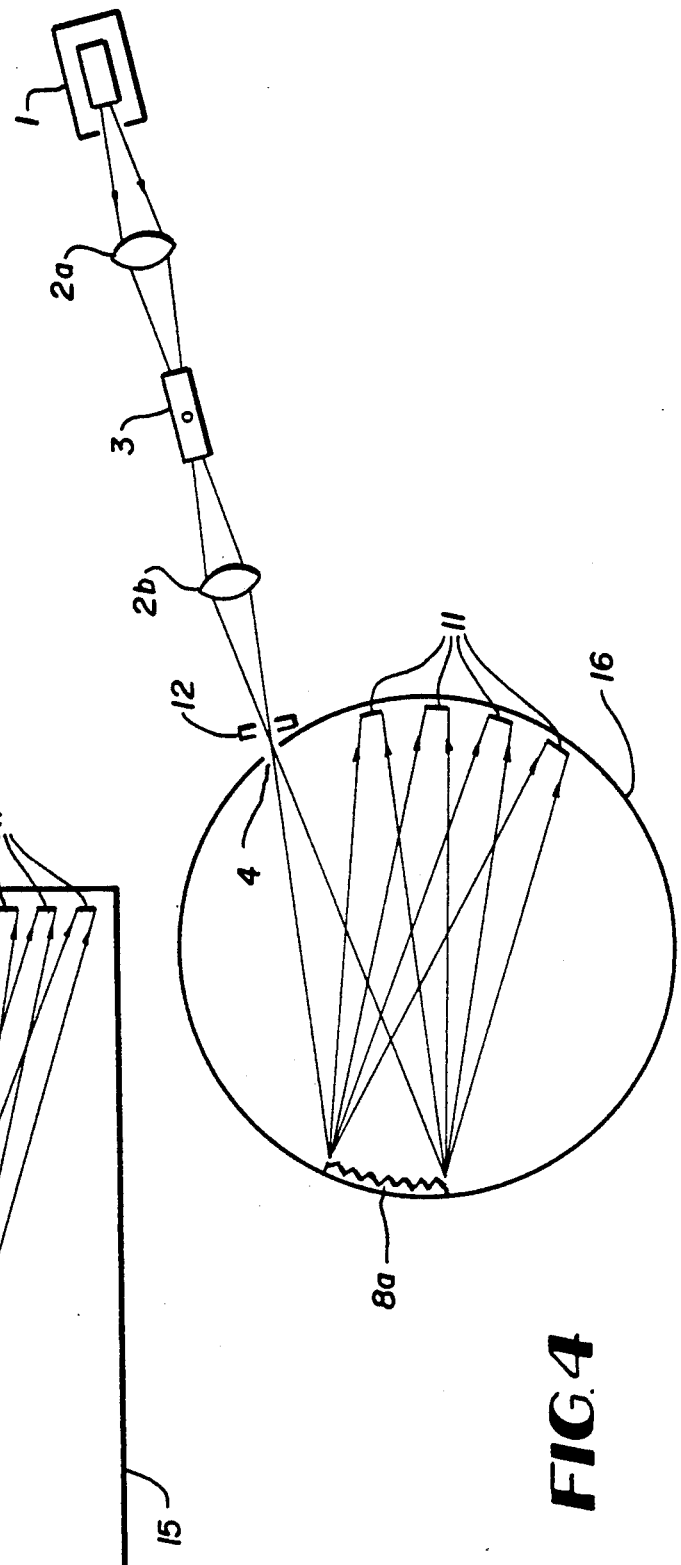
FIG. 4 shows a forth embodiment of the instant invention employing a Rowland circle configuration.

Certain of the foregoing light dispersing elements (e.g. the collimating mirror, prism, grating, and focusing mirror) and their interrelationship, are essentially the same as disclosed in U.S. Pat. No. 4,049,353 issued Sept. 20, 1977 to Missio. Alternatively to the embodiment of FIG. 1, various other light dispersing means and IADM arrangements may be utilized in the present invention. Examples of such alternative systems are illustrated in FIGS. 2 to 4. For the sake of simplification of illustration the computer and amplifier are not shown in FIGS. 2-4, however it should be understood that the computer and amplifier as described in connection with FIG. 1 are utilized with the systems of FIGS. 2-4. Elements of FIGS. 2 to 4 which are essentially the same as elements of FIG. 1, are designated by the same numeral utilized in FIG. 1.

The embodiment of FIG. 2 shows a plasmarray spectrometer designated 14, which includes light dispersing elements essentially as described in "Imaging Systems: Detectors of the Past, Present and Future" by Scott W. McGeorge in Spectroscopy Vol. 2, No. 4 1987 page 26 onward. This embodiment differs from the embodiment of FIG. 1 in that the light is predispersed in a conventional manner (grating 8a) and only specific wavelength regions are transmitted through the mask 13. The transmitted regions are then recombined by mirror 5a, and grating 8b. Subsequently the light is separated with an Echelle grating 7, and focused by mirror 5b onto a single IADM for detection without cross dispersion. The purpose of the mask is to limit the transmitted intensities to those wavelength regions of interest, and thus only a single IADM may be utilized.

The embodiment of FIG. 3 includes light dispersing elements essentially as utilized in the "Corrected Loci" system as described in "Description of McPherson Optical Systems" (pages A1 and A2) from McPherson, Acton, Mass. This system is modified to include an array of IADMs.

The embodiment of FIG. 4 employs a Rowland circle configuration, with light directed from grating 8a to an array of IADMs.

Figure 5:
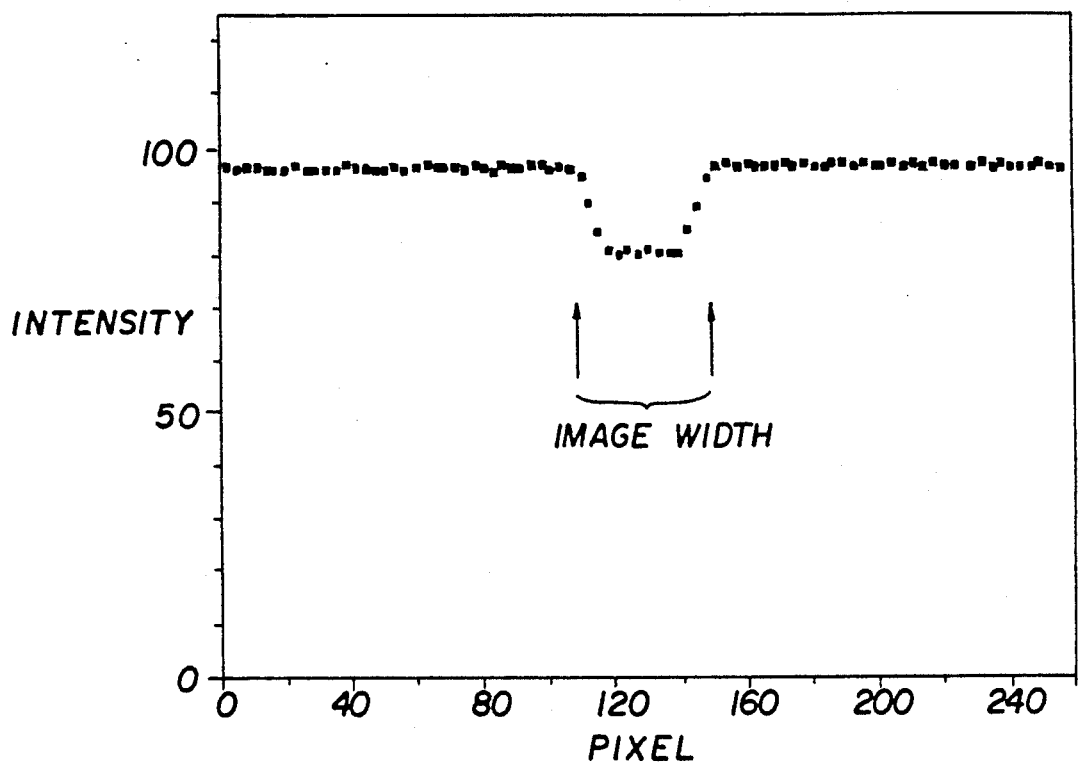
FIG. 5 is a graph of intensity (arbitrary units) v.s. pixel, depicting typical results for a single scan of a diode array.

FIG. 5 is a graph of intensity (in arbitrary units) v.s. pixels, illustrating typical results for a single scan of the diode array. The trapezoidal decrease in the intensity in the middle of the array represents the desired image of an element of interest. The image width is defined as the maximum width of the trapezoidal decrease i.e. measured from base line to base line. The image width at the exit plane of the dispersing means is equivalent to the width of the entrance slit. The diode must cover a length of about 4 to about 10 (preferably about 6 to about 10) times the image width. The intensity data from such a scan as FIG. 5 will be processed to produce signals which are linear with respect to the concentration of the element. This output will be obtained at least 40 times per second for each element.

Figure 6:
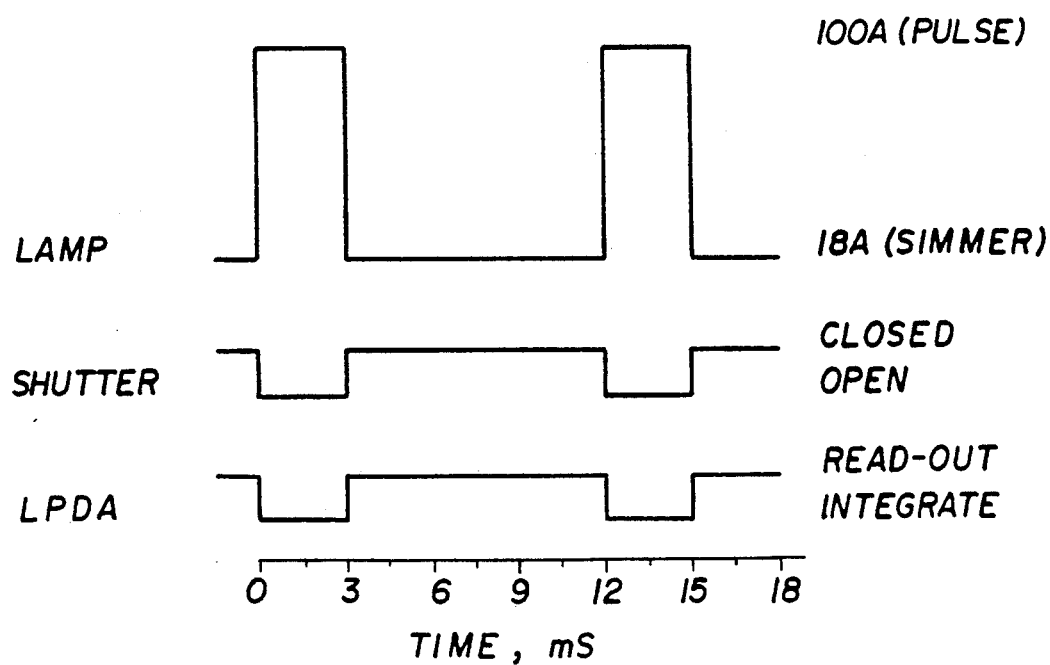
FIG. 6 is a timing diagram showing correlation of operation of: a continuum light source means i.e. CLSM, the means for blocking (e.g. a shutter) and the integrating array detector means i.e. IADM.

FIG. 6 is a diagram illustrating operation of the lamp, shutter and IADM of the aforementioned embodiments. A computer 17 may be utilized: (1) as control means (operably associated, as for example by electronic connection, with the aforementioned means for blocking, the IADM and the continuum light source means) to control operation of the aforementioned elements; (2) for signaling the IADM to readout and for receiving (and storing) from the IADM readout which is amplified electrical signals proportional to the integrated intensities, and; (3) deriving a value (i.e. deriving means) proportional to concentration and independent of the intensity as a function of time and wavelength. In the burst mode, the xenon arc lamp is operated at a moderate current (18–25 amps) for two to three minutes and then for 10–15 seconds is given a burst, or series, of short, high current (50–100 amps) pulses by means (operably associated with the CLSM) for intermittently increasing amperage of electricity directed to the CLSM. This provides light intensity from the CLSM at a high level which is above the normal intensity level of the CLSM (e.g. up to about 250 times the normal intensity level). During the burst period, the maximum power level of the lamp is exceeded by 40–80%. Each pulse lasts 1–5 msec. with 9–10 msec. between pulses, a high duty cycle of 10–30%. The emitted peak intensity of the lamp increases with current raised to the 2.3 power at the 200 nm wavelength. The average intensity for the whole pulse cycle is significantly enhanced compared to operation at the maximum current in the continuous mode. Use of short, high amperage pulses for a xenon arc lamp results in a shift in the spectral distribution of the output and an increased intensity in the far UV (180–270 nm). As the lamp is pulsed from the simmer current the shutter is opened and the intensity is summed at all wavelengths by each of the IADMs. The IADMs are used to integrate the lamp intensity over the pulse duration and are read out in the 9–10 msec. between pulses. The simultaneous detection of the intensities over each restricted wavelength region by the arrays allows the high pulse to pulse variation (fluctuation noise) to be eliminated and a value derived which is proportional to concentration and independent of the intensity as a function of time and wavelength. The short photodiode arrays are read out very rapidly (34 usec. per pixel, less than 9 msec. for a 256 array) between the lamp pulses. Pulsing and read out are repeated a minimum of 50 times a second (an absorbance is computed for each pulse), sufficient time resolution to allow detection of the rapid, transient signals from an electrothermal atomizer. The computed values proportional to concentration remain constant regardless of the entrance slit width and the width of the profiles. At the termination of the pulse, the shutter is closed (as for example, in response to a signal from computer 17) and an amplified electrical signal which is proportional to the integrated intensity from each of the IADMs is sequentially readout by the computer 17 via amplifier 18 i.e. in response to a signal from the computer to the IADM, the IADM provides the readout to the computer via amplifier 18. Subsequently the computer 17 derives from the amplified electrical signals a value proportional to concentration and independent of the intensity as a function of time and wavelength. The lamp will be pulsed a minimum of 40 times per second.

The foregoing detailed descriptions and examples are given merely for purposes of illustration. Modifications and variations may be made therein without departing from the spirit and scope of the invention.

INDEX OF ELEMENTS DESIGNATED BY A NUMERAL

1.—Continuum Light Source Means (CLSM)
2a.—Lens
2b.—Lens
3.—Atomizing Means
4.—Entrance Slit
5a.—Collimating Mirror
5b.—Collimating Mirror
6.—Prism
7.—Echelle Diffraction Grating
8.—Focusing Mirror
8a.—Grating
8b.—Grating
9.—Exit Cassette
10.—Disperser/Detector (Echelle Polychromator)
11.—Integrating Array Detector Means (IADM)
12.—Shutter
13.—Mask
14.—Plasmarray Spectrometer
15.—Corrected Loci Spectrometer (McPherson)
16.—Rowland Circle
17—Computer
18.—Amplifier

We claim:

1. A method for atomic absorption analysis, comprising the steps of:
   atomizing a sample to be analyzed;
   illuminating the atomized sample with a continuum light source means for emitting intensities from about 180 to about 800 nm, to produce a resultant light;
   directing said resultant light through a light dispersing means onto a focal plane of said light dispersing means, thereby providing images each having an image width;
   detecting light simultaneously at more than one wavelength at said focal plane of said light dispersing means using an integrating array detector means for integrating with respect to time the amount of light incident on said integrating array detector means and for converting the incident light into amplified electrical signals proportional to the integrated intensities of the incident light, said integrating array detector means spanning a small wavelength region of about 4 to about 10 times a said image width;
   blocking said incident light from striking said detector means,
   during said step of blocking utilizing said detector means to convert integrated intensities of incident light into amplified electrical signals which are proportional to said integrated intensities;
   deriving from said amplified electrical signals a value, proportional to concentration, and independent of intensity, and;
   repeating said steps of blocking and converting at a rate of at least 40 times per second.

2. The method of claim 1 further comprising the step of acquiring and storing data corresponding to said amplified electrical signals.

3. The method of claim 1 further including the steps of:
   providing plural integrating array detector means,
   directing dispersed light from said light dispersing means which includes a plurality of wavelength regions to said plural integrating array detector means, such that each said wavelength region is directed to one of said integrating array detector means.

4. The method of claim 1 including the step of intermittently increasing amperage of electricity directed to said continuum light source at a rate of at least 40 times per second to provide light intensity from said source at a high level which is above a normal intensity level of said source.

5. The method of claim 4 wherein said high level is up to about 250 times the intensity of said normal intensity level.

6. The method of claim 4 wherein said steps of blocking, converting and intermittenly increasing amperage, are repeated at a rate of at least 60 times per second.

7. The method of claim 6 wherein said steps of blocking, converting and intermittenly increasing amperage, are repeated at a rate of at least 80 times per second.

8. An apparatus for atomic absorption analysis, comprising:
   means for atomizing a sample to be analyzed;
   continuum light source means for illuminating said atomized sample with intensities from about 180 to about 800 nm;
   light dispersing means;
   light directing means for directing light from said continuum light source means through an atomized sample and into said light dispersing means onto a focal plane of said light dispersing means, thereby providing images each having an image width;
   integrating array detector means, located at said focal plane of said light dispersing means, for integrating with respect to time the amount of light incident on said integrating array detector means and for converting the incident light into amplified electrical signals proportional to the integrated intensities of the incident light, said integrating array detector means spanning a small wavelength region of about 4 to about 10 times a said image width;
   means for blocking said incident light from striking said detector means;
   control means, operably associated with said means for blocking and said integrating array detector means, for controlling said means for blocking and for signaling said integrating array detector means to readout and for receiving from said integrating array detector means readout which is amplified electrical signals proportional to said integrated intensities, while incident light is blocked from striking said detector means;

deriving means, operably associated with said integrating array detector means, for deriving from said amplified electrical signals a value, proportional to concentration, and independent of intensity, and; wherein said means for blocking and said control means function to provide their respective functions at a rate of at least 40 times per second.

9. The apparatus of claim 8 further including operably associated means for acquiring and storing data corresponding to said amplified electrical signals.

10. The apparatus of claim 8 wherein light dispersed by said dispersing means includes a plurality of wavelength regions and further including plural integrating array detector means positioned such that each said wavelength region is incident upon one of said integrating array detector means.

11. The apparatus of claim 8 further including means, operably associated with said continuum light source means, for intermittently increasing amperage of electricity directed to said continuum light source means at a rate of at least 40 times per second to provide light intensity from said continuum light source means at a high level which is above a normal intensity level of said continuum light source means.

12. The apparatus of claim 11 wherein said high level is up to about 250 times the intensity of said normal intensity level.

13. The apparatus of claim 11 wherein said means for blocking, said control means and said means for intermittently increasing amperage, function to provide their respective functions at a rate of at least 60 times per second.

14. The apparatus of claim 13 wherein said means for blocking, said control means and said means for intermittently increasing amperage, function to provide their respective functions at a rate of at least 80 times per second.

15. The apparatus of claim 8 wherein said means for atomizing is selected from the group consisting of an electrothermal furnace, a flame atomizer, or a plasma generator.

16. The apparatus of claim 15 wherein said means for atomizing is an electrothermal furnace.

* * * * *